United States Patent
Lee et al.

(10) Patent No.: US 12,303,708 B2
(45) Date of Patent: May 20, 2025

(54) MICROWAVE TREATMENT APPARATUS

(71) Applicant: Ion Medical Inc., Seongnam-si (KR)

(72) Inventors: Keunho Lee, Seoul (KR); Postel Olivier, Colorado Springs, CO (US)

(73) Assignee: Ion Medical Inc., Seongnam-si (KR)

( * ) Notice: Subject to any disclaimer, the term of this patent is extended or adjusted under 35 U.S.C. 154(b) by 578 days.

(21) Appl. No.: 17/501,086

(22) Filed: Oct. 14, 2021

(65) Prior Publication Data

US 2022/0152410 A1    May 19, 2022

(30) Foreign Application Priority Data

Nov. 19, 2020   (KR) .................. 10-2020-0155248

(51) Int. Cl.
*A61N 1/44* (2006.01)
*A61N 5/02* (2006.01)

(52) U.S. Cl.
CPC ............... *A61N 5/025* (2013.01); *A61N 1/44* (2013.01)

(58) Field of Classification Search
CPC . A61N 5/025; A61N 1/44; A61N 5/01; A61N 5/0616; A61N 5/0624; A61N 2005/0642; A61N 2005/0632; A61N 2005/0664; A61B 2018/048
See application file for complete search history.

(56) References Cited

U.S. PATENT DOCUMENTS

| | | | | |
|---|---|---|---|---|
| 5,085,219 A * | 2/1992 | Ortendahl | ........ | G01R 33/34007 324/318 |
| 6,104,959 A * | 8/2000 | Spertell | ..................... | A61N 5/04 607/101 |
| 2014/0200506 A1* | 7/2014 | Zemel | .................. | A61B 18/042 604/23 |
| 2015/0105716 A1* | 4/2015 | Ish-Yamini Tomer | ... | A61N 1/44 29/25.35 |

FOREIGN PATENT DOCUMENTS

| | | | |
|---|---|---|---|
| EP | 2599506 A2 * | 6/2013 | ........... A61B 18/042 |
| KR | 20110018018 A | 2/2011 | |
| KR | 20180092641 A | 8/2018 | |
| KR | 10-1927489 B1 | 12/2018 | |
| KR | 20190122176 A * | 5/2019 | |

* cited by examiner

*Primary Examiner* — Joanne M Rodden
*Assistant Examiner* — Dana Stumpfoll
(74) *Attorney, Agent, or Firm* — NKL LAW; Jae Youn Kim

(57) ABSTRACT

Disclosed is a microwave treatment apparatus which treats the surface of the skin or subcutaneous tissues using a combination among a microwave frequency electric field generated by microwaves, low-frequency electric spark discharge and low-temperature ionized gas flow.

1 Claim, 5 Drawing Sheets

MICROWAVE TREATMENT APPARATUS

CROSS-REFERENCE TO RELATED APPLICATION

This application claims priority to and the benefit of Korean Patent of Application No. 10-2020-0155248, filed on Nov. 19, 2020, the disclosure of which is incorporated herein by reference in its entirety.

BACKGROUND OF THE INVENTION

Field of the Invention

The present invention relates to a microwave treatment apparatus, more particularly, to a microwave treatment apparatus which treats the surface of the skin or subcutaneous tissues using a combination among a microwave frequency electric field generated by microwaves, low-frequency electric spark discharge and low-temperature ionized gas flow.

Description of the Related Art

The skin is a layer covering the surface of the body of an animal, and has not only a physiological function of protecting the body but also a social function of expressing the appearance, feelings, etc. of an individual.

The skin greatly affects the impression of the individual, as described above, and thus, interest in skin care is gradually increasing recently.

Therefore, various technologies for skin treatment are being developed and, for example, Patent Documents 1 to 3 disclose these technologies.

Patent Document 1 discloses a portable skin treatment device configured to perform a function of radiating light and heat, the portable skin treatment device having a housing configured to have a control button, a display unit and a skin contact tip, a printed circuit board located in the housing including a heater configured to heat the tip and a heater controller configured to control the heater, a microcomputer controller configured to control operation of the light source treatment device radiating light to the outside through the tip, and a power supply configured to supply power, and an LED adhered to the edge surface of the end of the printed circuit board adjacent to the tip being used as a light source.

Patent Document 2 discloses a support structure for a handpiece of a skin treatment apparatus, configured to support the handpiece the handpiece used in the state of being contact with the skin and cables connecting the handpiece to a control main body configured to control operation of the handpiece, the support structure including cable holder housings through which the cables pass, cable length adjusters located within the cable holder housings and configured to selectively fix or move the positions of the cables, each of the cable length adjusters including a cable support member provided with a mount part on which the cable is seated, an elastic stopper configured to protrude from the upper surface of the cable support member and inserted into thread grooves of the cable in an elastically supported state, a base support member located under the cable support member and combined therewith so as to move the cable support member upwards and downwards, support spring members located between the base support member and the cable support member so as to elastically support the cable support member, and a stopper release switch member located on the cable support member and exposed to the outside of the cable holder housing.

Patent Document 3 discloses a fractional plasma skin therapy apparatus including an operator configured to come into contact with the surface of the skin and provided with needles moved upwards so as to be inserted into the skin and thus to transmit high frequencies into the tissues of the skin, a handpiece combined with the rear end of the operator and configured to convert power into power for generating high-frequency and high-voltage plasma through a high-voltage module and to transmit the power for generating high-frequency and high-voltage plasma to the operator, the operator including a main body having a hollow shape, the lower part of which is open, and including a plurality of guide pipes provided on the upper surface of the main body coming into contact with the skin so as to be spaced apart from one another by a predetermined distance, and including needle center holes provided in the inner circumferential surfaces of the guide pipes so as to have the same diameter as the outer diameter of the needles and thus to support the needles so as to locate the needles at the centers of the respective guide pipes, and an elevator combined with the inside of the main body so as to be slidable, provided with the needles corresponding to the guide pipes on the upper surface of the elevator, and configured to ascend so as to expose the needles upwards from the upper surfaces of the guide pipes.

The above-described various skin treatment technologies have been developed, but these technologies use only heat or high frequencies and thus have a drawback in that curative effects are low.

RELATED ART DOCUMENT

Patent Document (Patent Document 0001) Korean Patent Registration No. 10-1193527
(Patent Document 0002) Korean Patent Registration No. 10-1927489
(Patent Document 0003) Korean Patent Registration No. 10-2069290

SUMMARY OF THE INVENTION

Therefore, the present invention has been made in view of the above problems, and it is an object of the present invention to provide a microwave treatment apparatus which may treat the surface of the skin or subcutaneous tissues using various stimuli depending on the state of the skin or the subcutaneous tissues.

It is another object of the present invention to provide a microwave treatment apparatus which treats the surface of the skin or subcutaneous tissues using a combination among a microwave frequency electric field generated by microwaves, low-frequency electric spark discharge and low-temperature ionized gas flow.

In accordance with the present invention, the above and other objects can be accomplished by the provision of a microwave treatment apparatus configured to treat skin or subcutaneous tissues, the microwave treatment apparatus including an electrode configured to generate microwaves by electricity received from a power supply, a chamber configured to have a hollow tubular form and installed at a central region of the microwave treatment apparatus so as to expose one end of the electrode towards the skin, and a gas supply source configured to supply gas to a space between the electrode and an inner wall of the chamber, wherein the supplied gas is converted into low-temperature ionized gas by an electric field having frequencies of the microwaves generated by the electrode, and the ionized gas is supplied to the skin so that the skin is exposed to the ionized gas.

A temperature of the ionized gas may be 50° C.

A treated region of the ionized gas may have a depth of less than 10 mm.

A flow velocity of the ionized gas may be repeatedly modulated from a low level to a high level with a period of 0.0001-10 Hz.

A subsidiary gas supply source may be further provided at one side of the microwave treatment apparatus.

Gas supplied by the subsidiary gas supply source may be supplied periodically.

At least one light source configured to radiate light to the skin may be further provided at one side of the microwave treatment apparatus. The at least one light source may be installed on a light source holder integrated with one side of the chamber.

The at least one light source may be installed at one end of the chamber opposite to the skin, a light-transmitting glass plate may be installed at the end of the chamber, and a lens may be installed between the at least one light source and the light-transmitting glass plate.

The microwave treatment apparatus may be installed in a treatment apparatus holder, the treatment apparatus holder may be installed to be supported by an assembly base so as to be movable vertically and to be movable horizontally in an arc shape, the treatment apparatus holder may be installed so as to be movable horizontally in the arc shape along an arc-shaped rail, and elevating slides may be installed at both ends of the arc-shaped rail so as to move the treatment apparatus holder vertically, and may be combined with an open front part of the assembly base provided with an inner space, configured such that a human body is placed therein, so as to be movable vertically.

BRIEF DESCRIPTION OF THE DRAWINGS

The above and other objects, features and other advantages of the present invention will be more clearly understood from the following detailed description taken in conjunction with the accompanying drawings, in which.

DETAILED DESCRIPTION OF THE INVENTION

Figure 1:
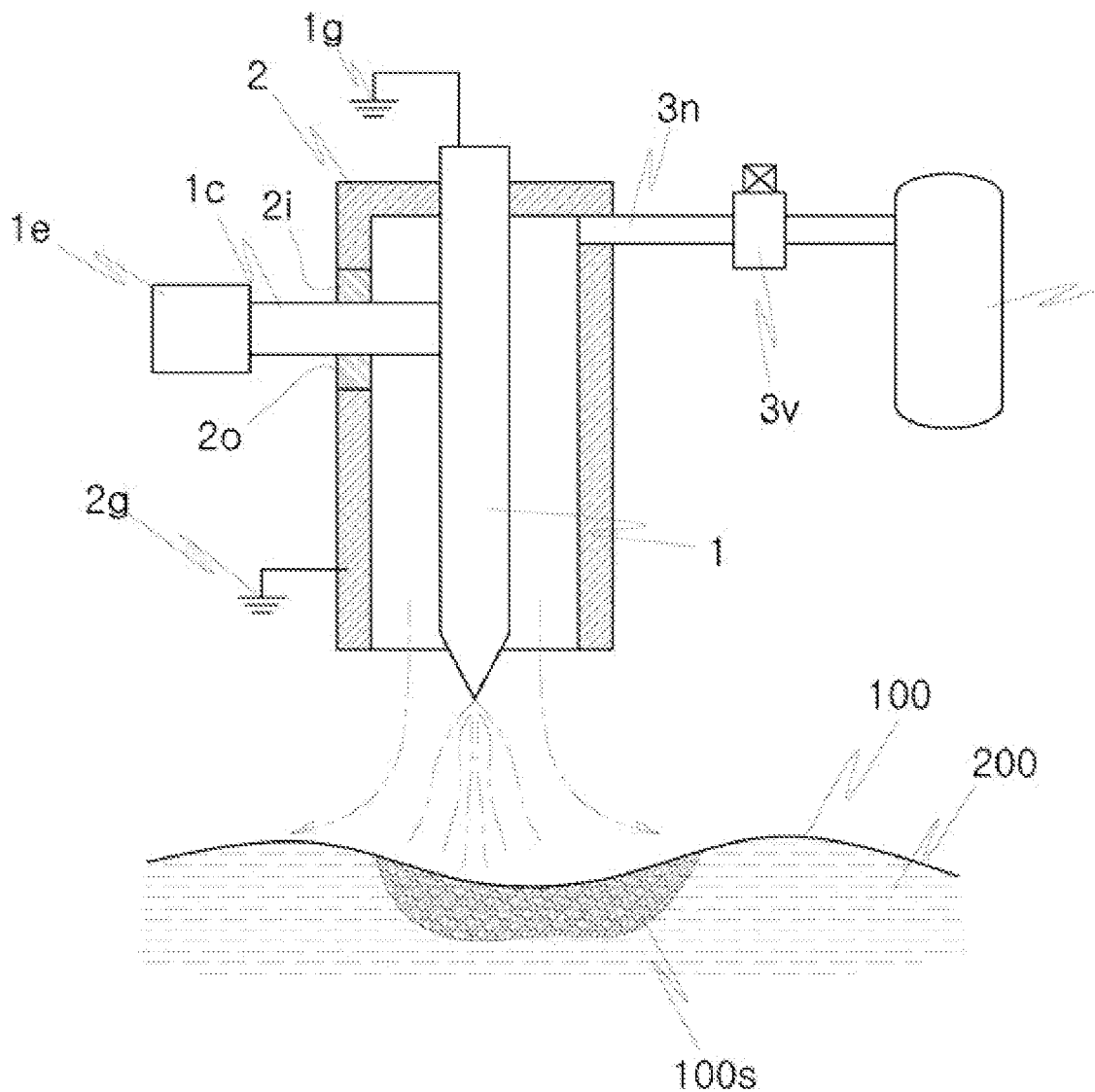
FIG. 1 is a longitudinal-sectional view of a microwave treatment apparatus according to one embodiment of the present invention.

Hereinafter reference will be made in detail to various embodiments of the present invention, examples of which are illustrated in the accompanying drawings and described below. While the invention will be described in conjunction with exemplary embodiments, it will be understood that the present description is not intended to limit the invention to the exemplary embodiments. On the contrary, the invention is intended to cover not only the exemplary embodiments, but also various alternatives, modifications, equivalents and other embodiments, which may be included within the spirit and scope of the invention as defined by the appended claims.

In the drawings, the same or similar elements are denoted by the same reference numerals even though they are depicted in different drawings. In the following description of the present invention, a detailed description of known functions and configurations incorporated herein will be omitted when it may make the subject matter of the present invention rather unclear The present invention is configured to treat the surface of the skin or subcutaneous tissues using various types of stimuli.

Figure 2:
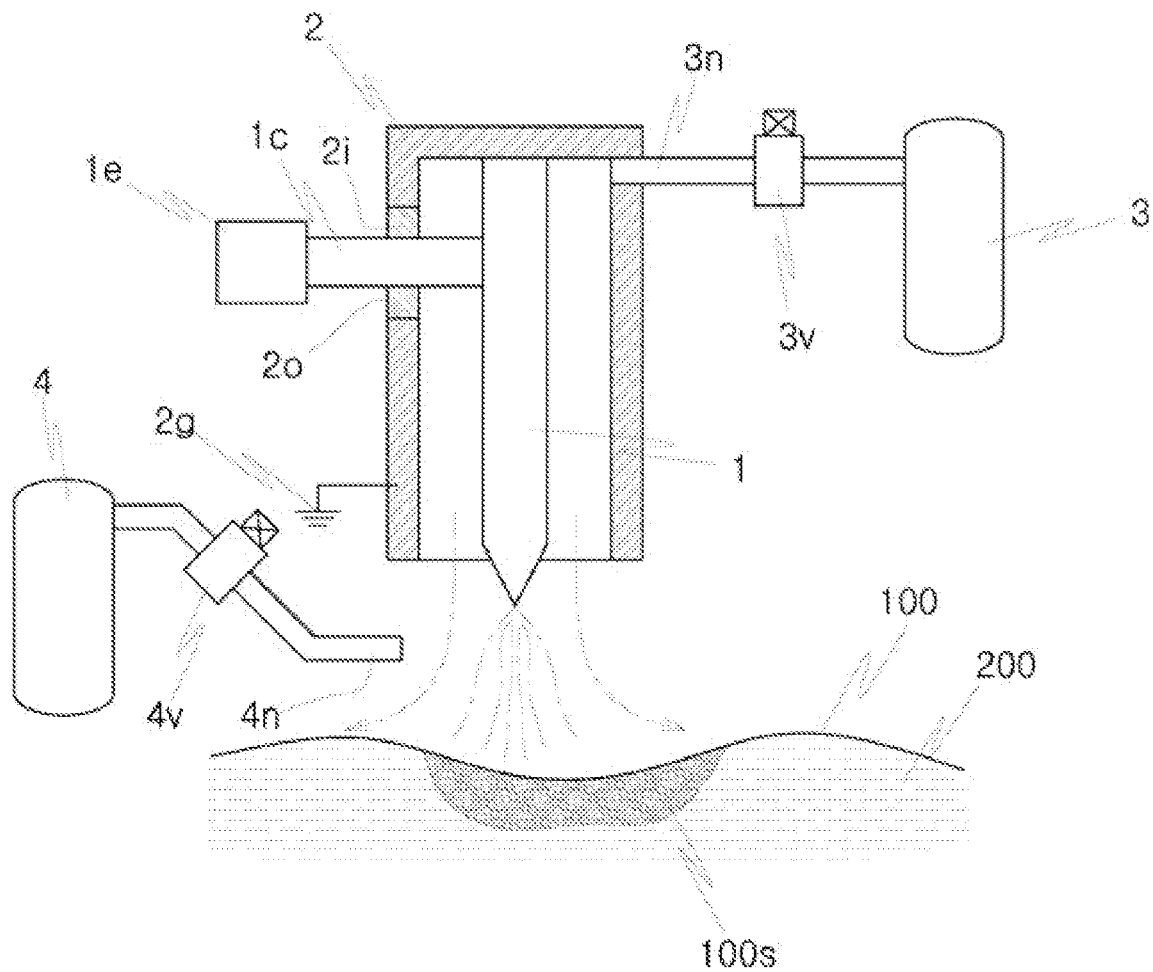
FIG. 2 is a longitudinal-sectional view of a microwave treatment apparatus according to another embodiment of the present invention.
Figure 3:
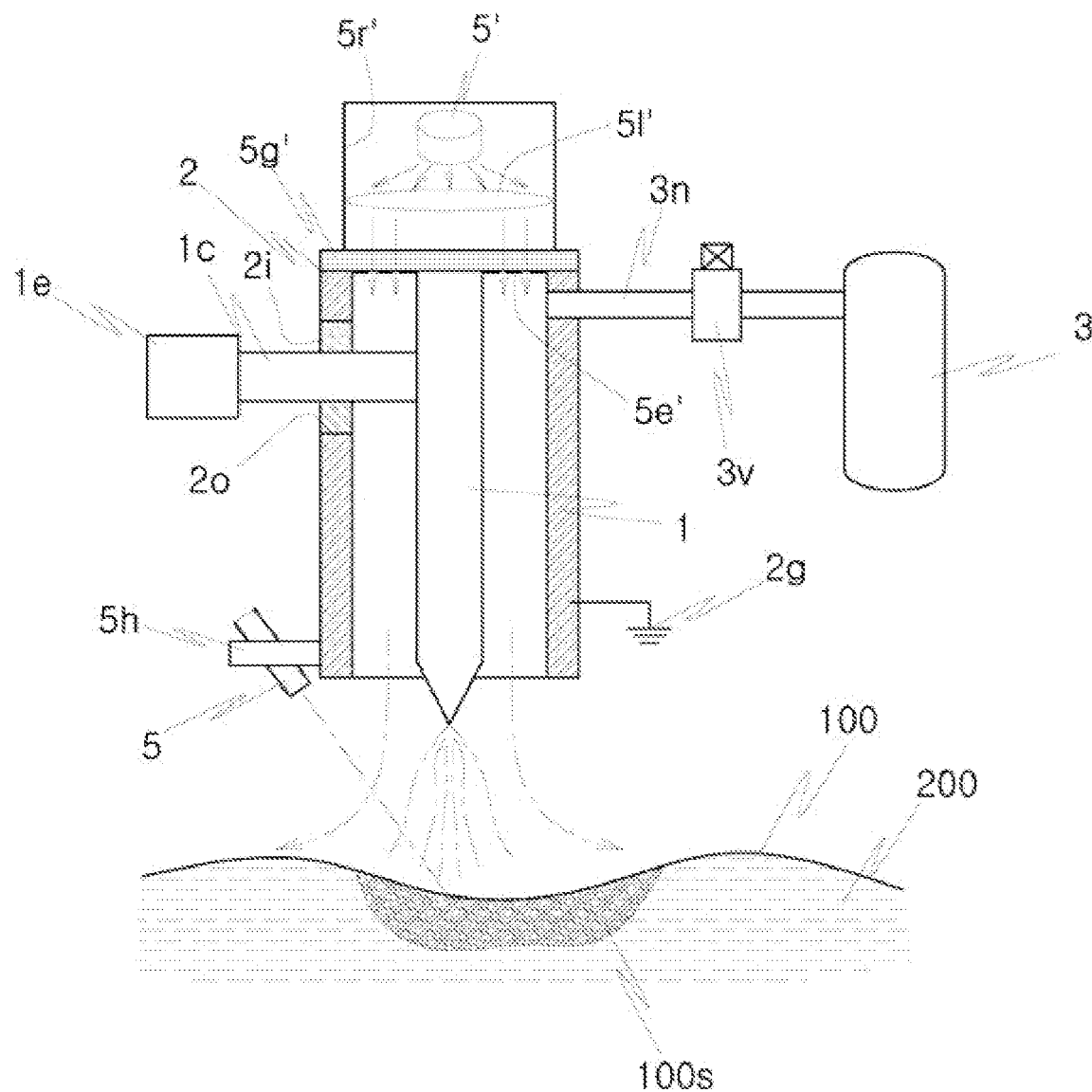
FIG. 3 is a longitudinal-sectional view of a microwave treatment apparatus according to yet another embodiment of the present invention.

A microwave treatment apparatus according to the present invention is an apparatus which treats the surface of skin 100 or subcutaneous tissues 200, as shown in FIGS. 1 to 3, and includes an electrode 1 configured to generate microwaves by electricity received from a power supply 1e, a chamber 2 configured to have a hollow tubular form and installed at the central region of the microwave treatment apparatus so as to expose one end of the electrode 1 towards the skin 100, and a gas supply source 3 configured to supply gas to a space between the electrode 1 and the inner wall of the chamber 2, the supplied gas is converted into low-temperature ionized gas by an electric field having the frequencies of the microwaves generated by the electrode 1, and the ionized gas is supplied to the skin 100 so that the skin 100 is exposed to the ionized gas.

The electrode 1 generates the electric field having frequencies that may stimulate and activate the skin 100 or the subcutaneous tissues 200, by electricity received from the power supply 1e, and is formed as a rod having one sharp end.

The electrode 1 may be formed of any one of various metals, may be manufactured as a hard tubular shape, and may have a greater length than the length of the chamber 2 so that the sharp end of the electrode 1 protrudes from a corresponding end of the chamber 2.

The electrode 1 is grounded (1g).

Further, as shown in FIGS. 1 to 3, the electrode 1 may be located on the central line of the center of the chamber 2, one end of the electrode 1 may protrude from an open end of the chamber 2, and the other end of the electrode 1 may pass through the other end of the chamber 2 and protrude therefrom (with reference to FIG. 1) or may be fixed to the closed end of the chamber 2 (with reference to FIGS. 2 and 3).

The electrode 1 is connected to the power supply 1e by a conductor 1c including an electric wire, the conductor 1c passes through an opening 2o formed through the side wall of the chamber 2 and is connected to the electrode 1, and an insulator 2i is installed in the opening 2o so as to perform electrical insulation.

The chamber 2 is manufactured as a tubular form provided with at least one open end.

The chamber 2 may be formed of a metal, and may be grounded (2g) considering that electric leakage may occur due to electricity supplied from the power supply 1e.

The inner space of the chamber 2 may have a greater diameter than the diameter of the electrode 1 so that gas introduced into the chamber 2 may smoothly flow.

The open end of the chamber 2 faces the skin 100, and must maintain a designated distance D from the skin 100.

A treatment apparatus assembly including the chamber 2 and the skin 1 may be used as a handheld apparatus, and thus, in accordance a preferred embodiment, may be connected to the power supply 1e and the gas supply source 3 by members formed of a flexible material so that the assembly may be easily moved along the skin 100.

That is, the conductor 1c between the power supply 1e and the electrode 1 and a gas supply line between the gas supply source 3 and the chamber 2 may be flexible.

The gas supply source 3 serves to supply gas to be ionized by microwaves generated by the electrode 1, and the gas supply line is provided between a nozzle 3c coupled to one side of the chamber 2 and the gas supply source 3, as shown in FIG. 1, and in this case, the gas supply line may be formed of a soft material so as to allow the chamber 2 to be freely movable.

A valve 3v may be installed at one side of the nozzle 3n so as to control the flow rate of gas supplied to the nozzle 3n, and when the valve 3v is open, the gas flows into the inner space of the chamber 2 through the nozzle 3n.

The gas may flow into the chamber 2 at a flow velocity of 0.1-20 s/m, and the gas supplied to the inside of the chamber 2 is discharged to the outside through the open end of the chamber 2 so as to stimulate the skin 100.

The power supply 1e supplies power of microwave frequencies of 1-50 GHz to the electrode 1. The level of the microwave power may be constant or be periodically modulated, and may be modulated in the range of 10-100 W.

As described above, the inner space of the chamber 2 serves as a microwave resonance cavity. That is, an electric field having a high strength is formed at the protruding end of the electrode 1, and thus causes electrical breakdown and ionization of gas around the end of the electrode 1.

The ionized gas due to gas flow between the chamber 2 and the electrode 1 generates low-frequency plasma streamers, and thereby, the gas is highly ionized but is not thermally heated and thus the temperature of the gas is low, i.e., is equal to or less than about 50° C.

An area influenced by the ionized gas may be increased as the flow velocity of the gas and the microwave power are increased. When the flow velocity of the gas is increased, the temperature of the gas is decreased. The flow of the ionized gas is reduced at a distance downwards from the end of the electrode 1 by 2-3 cm.

The microwave treatment apparatus according to the present invention is disposed at a distance D1 from the skin 100, which is shorter than the length of a light emitting portion of the ionized gas flow.

D1 is in the range of 5-30 mm, the center of the chamber 2 may be oriented vertically to the surface of an object to be treated in a preferred embodiment, and the skin 100 and subcutaneous tissues 200 inside a treated region 100s under the footprint of the ionized gas flow on the skin 100 are simultaneously treated by the following factors.

That is, ozone, oxygen atoms and hydroxyl radicals are formed in the ionized gas flow, and thus attack bacteria on the skin 100 so as to disinfect the skin 100. The ionized gas emits ultraviolet light having a wavelength range of 430-500 nm which is known to have a sterilizing effect.

The ionized plasma streamers between the electrode 1 and the subcutaneous tissues 200 cause low-current and low-frequency electrical discharge which activates nerves in the subcutaneous tissues 200 inside the treated region 100s and improves blood circulation and muscle tension. Current of all discharges is less than 5 microamperes ($\mu$A), which causes weak pain, and thus, the plasma streamers produce only a sense of "mild tingling".

FIG. 2 illustrates a microwave treatment apparatus according to another embodiment of the present invention, and in this embodiment, the microwave treatment apparatus may further include a subsidiary gas supply source 4.

The subsidiary gas supply source 4 is configured to supply gas like the gas supply source 3, and may be provided with a nozzle 4n disposed at a position adjacent to the open end of the chamber 2, and the outlet of the nozzle 4n heads for the central axis of the chamber 2 in a region between the electrode 1 and the skin 100, and more particularly, heads for the intersection between the skin 100 and the central axis of the chamber 2.

A valve 4v is provided on a gas line between the nozzle 4n and the subsidiary gas supply source 4 so as to control the flow of compressed gas.

Further, the microwave treatment apparatus according to the present invention may further include light sources 5 and 5'.

The light sources 5 and 5' may be installed on the chamber 2 by a light source holder 5h or be installed at the closed end of the chamber 2, as shown in FIG. 3.

The light sources 5 and 5' may be lamps, laser light sources, optical fiber light sources or any other random known light sources, and light emitted by the light sources 5 and 5' is radiated towards the skin 100.

In a preferred embodiment, light radiated by the light sources 5 and 5' forms a pointer heading for the intersection between the central axis of the chamber 2 and the skin 100.

Among the two light sources 5 and 5', the light source 5' installed at the closed end of the chamber 2 may be configured such that a light-transmitting glass plate 5g' is installed at the end of the chamber 2 and a lens 5l' is installed between the light source 5' and the light-transmitting glass plate 5g', as shown in FIG. 3.

That is, the light-transmitting glass plate 5g', which transmits light, does not transmit microwave frequencies and blocks an electric field and compressed gas, may be used at the closed end of the chamber 2 so as to prevent leakage of the electric field and the compressed gas, and the light-transmitting glass plate 5g' may be covered with a metal mesh or an electrically conductive transparent film grounded via the wall of the chamber 2 or electrically connected to the wall of the chamber 2, for example, a protective strip 5e' formed of an electrically conductive material, such as $SnO_2$.

The electrode 1 may be electrically connected to the protective strip 5e', and the light source 5' may emit light capable of passing through the lens (called "an optical system") 5l' so as to form a light beam parallel to the central axis of the chamber 2.

Further, the light source 5' may be installed in a tubular body formed of a reflective mirror 5r'.

Figure 4:
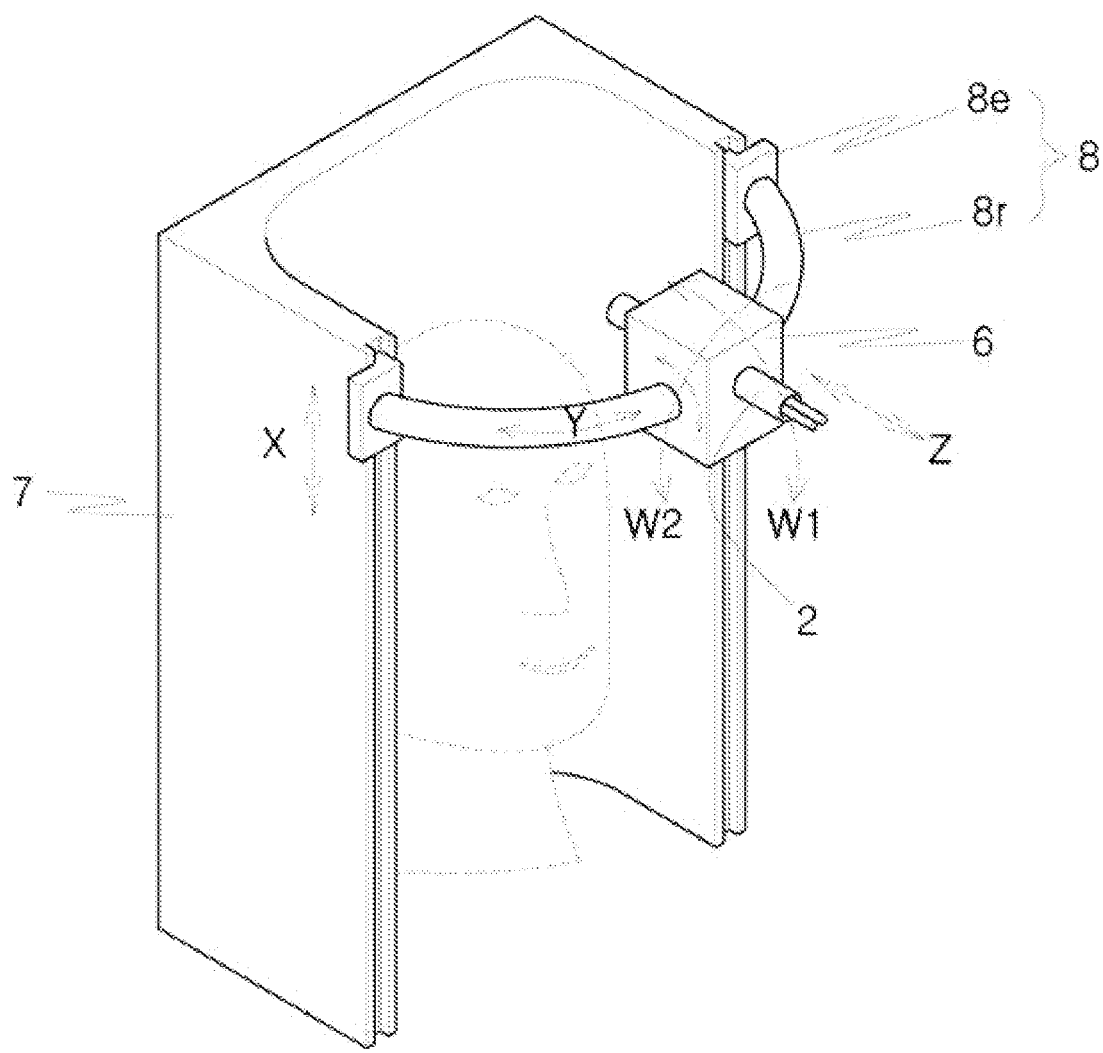
FIG. 4 is a perspective view illustrating the microwave treatment apparatus according to the present invention installed on an assembly base.
Figure 5:
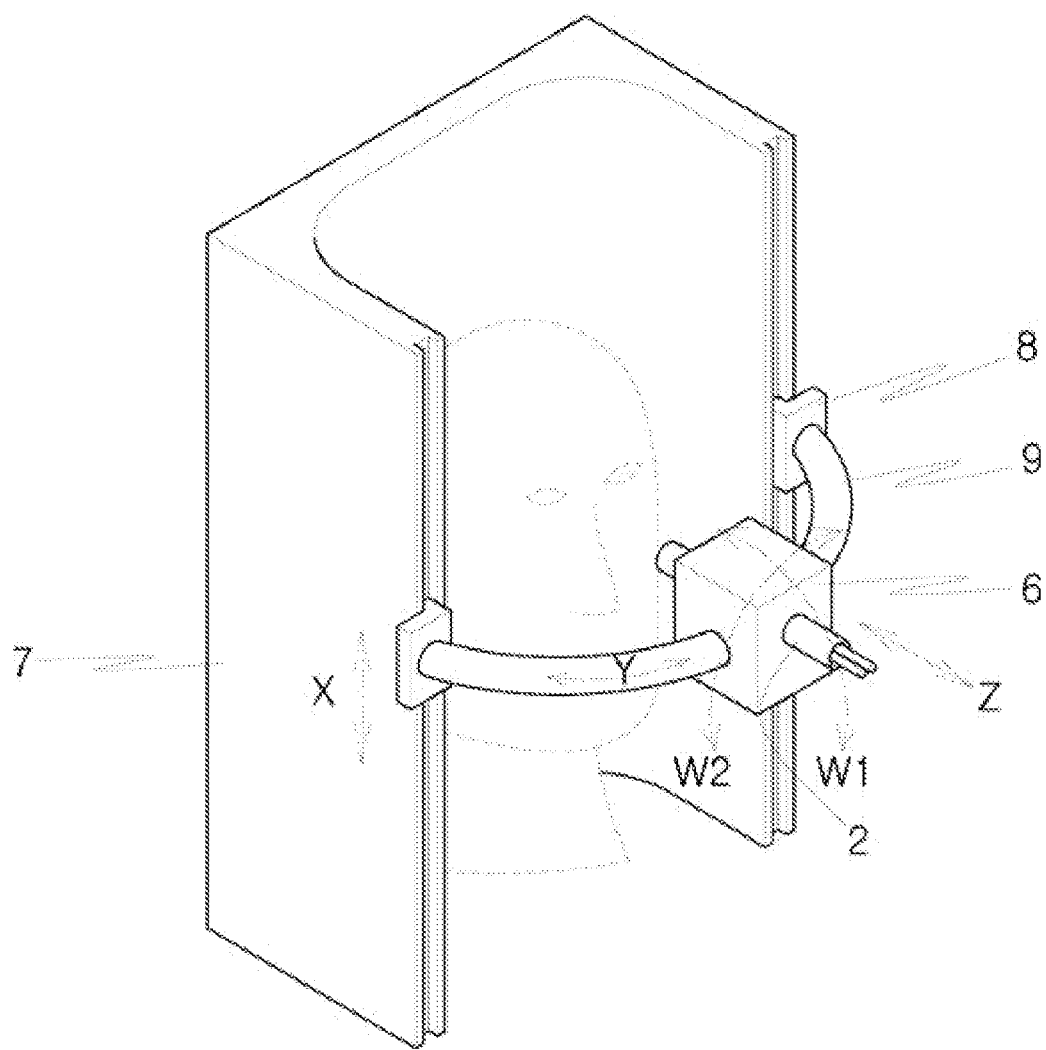
FIG. 5 is a perspective view illustrating the operating state of the microwave treatment apparatus according to the present invention installed on the assembly base.

Moreover, in the microwave treatment apparatus according to the present invention, the electrode 1 and the chamber 2 may be installed on a robot platform 8 mounted on an assembly base 7, as shown in FIGS. 4 and 5.

The assembly base 7 is formed as a tubular form, one surface of which is open, so that a human body is placed therein, the robot platform 8 is installed at the edges of the open surface of the assembly base 7, a treatment apparatus holder 6 is installed on the robot platform 8, the chamber 2 is installed in the treatment apparatus holder 6, and thereby, the treatment apparatus holder 6 is supported by the assembly base 7 so as not only to be moved up, down, left and right but also to be tilted.

That is, the robot platform 8 may control movement of the assembly at least two-dimensionally.

In other words, the robot platform 8 may be moved three-dimensionally in the x-axis, y-axis and z-axis directions, and the treatment apparatus holder 6 has a function of tilting the chamber 2 in the upward and downward directions and in the leftward and rightward directions.

The robot platform 8 is configured such that the treatment apparatus holder 6 is installed on an arc-shaped rail 8r which traverses a patient's body part and moves the chamber 2 in an arc-shaped trajectory (in the Y-axis direction), and is electrically slid so as to move the treatment apparatus holder 6 while traversing the patient's body part.

Further, elevating slides 8e are installed at the ends of the arc-shaped rail 8r so as to be movable in the upward and downward directions of the patient's body part (i.e., in the X-axis direction), and thus, the treatment apparatus holders 6 is moved upwards and downwards together with upward and downward movement of the arc-shaped rail 8r, and thereby, the microwave treatment apparatus including the chamber 2 may be moved in the upward and downward directions and in the leftward and rightward directions.

Further, the treatment apparatus holder 6 may move the chamber 2 horizontally so that a required distance between the chamber 2 and the skin of the patient's body part may be maintained, and the chamber 2 may be electrically controlled to be tilted so that the outlet of the chamber 2 may remain vertical to the skin of the patient's body part.

Hereinafter, the operation of the above-described microwave treatment apparatus according to the present invention will be described in detail.

Compressed gas from the gas supply source 3 is transmitted to the chamber 2 via a fluid channel and the valve 3v.

The gas may be supplied to the chamber 2 at a flow velocity of 0.1-20 s/m, and the gas is discharged to the outside through the open end of the chamber 2.

The power supply 1e supplies power of microwave frequencies of 1-50 GHz to the electrode 1 through the conductor 1c. The level of the microwave power may be constant or be periodically modulated, and may be modulated in the range of 10-100 W.

The inner space of the chamber 2 may serve as a microwave resonance cavity, an electric field having a high strength is formed at the protruding end of the electrode 1 and thus causes electrical breakdown and ionization of gas around the end of the electrode 1, and the ionized gas flow generates low-frequency plasma streamers.

The gas is highly ionized but is not thermally heated, and thus the temperature of the ionized gas is low, i.e., about 50° C., and the size (active area) of the ionized gas flow is increased as the flow velocity of the gas and the microwave power are increased.

When the flow velocity of the gas is increased, the temperature of the gas is decreased, and the ionized gas flow is reduced at a distance downwards from the end of the electrode 1 by 2-3 cm.

The microwave treatment apparatus is disposed at a distance D1 from the skin 100, which is shorter than the length of the light emitting portion of the ionized gas flow. D1 is in the range of 5-30 mm. The center of the chamber 2 may be oriented vertically to the surface of an object to be treated in a preferred embodiment, and the skin 100 and the subcutaneous tissues 200 inside the treated region 100s under the footprint of the ionized gas flow on the skin 100 are simultaneously treated by the following factors.

That is, ozone, oxygen atoms and hydroxyl radicals are formed in the ionized gas flow, and thus attack bacteria on the skin 100 so as to disinfect the skin 100. The ionized gas emits ultraviolet light having a wavelength range of 430-500 nm which is known to have a sterilizing effect.

The ionized plasma streamers between the electrode 1 and the skin 100 cause low-current and low-frequency electrical discharge which activates nerves in the subcutaneous tissues 200 inside the treated region 100s and improves blood circulation and muscle tension, and current of all discharges is less than 5 microamperes (μA) which cause weak pain, and thus, the plasma streamers produce only a sense of "mild tingling".

The energy of microwaves transmitted from the electrode 1 is transmitted to the treated region 100s through the ionized gas flow so as to heat the subcutaneous tissues 200.

Rise in the temperature of the subcutaneous tissues 200 varies depending on the microwave power supplied by the power supply 1e, microwave frequencies, the moisture content of the subcutaneous tissues 200, and the residence time of the microwave treatment apparatus on a given skin region.

A small change in the distance between the electrode 1 and the skin 100 does not greatly affect transmission of the microwave energy through the ionized gas flow, and therethrough, contactless treatment of the skin 100 using microwaves is possible and a skin treatment process is dramatically simplified because there is no accurate positioning requirement.

Heating of the subcutaneous tissues 200 is known to exhibit an anti-inflammatory effect assisting in acne treatment, and local mild heat may improve blood circulation and muscle tension.

In another embodiment, the flow velocity of the compressed gas may be periodically adjusted by partially closing or opening the valve 3v, and in this case, the low flow velocity level of the compressed gas may be within the range of about 0.1-3 s/m, the high flow velocity level of the compressed gas may be within the range of about 5-10 s/m, and a frequency which is the reciprocal of the period is 0.001-10 Hz. Thereby, undesired heating of the surface of the skin 100 due to convective heat flux from the ionized gas flow may be minimized, and gas in the gas supply source 2 may be conserved.

In another embodiment, the subsidiary gas supply source 4 supplies subsidiary gas to the ionized gas flow through the nozzle 4n, and in this case, the subsidiary gas is supplied as a pulse by periodically opening and closing the valve 4v. The flow velocity of the subsidiary gas is 1-10 s/m, and a pulse duration is 0.5-5 sec. Supply of the subsidiary gas reduces convective heating of the surface of the skin 100, but does not greatly affect microwave heating of the subcutaneous tissues 200. In a preferred embodiment, the subsidiary gas flow heads for the skin 100 under the footprint of the ionized gas flow on the skin 100. The subsidiary gas flow colliding with the skin 100 and flowing along the skin 100 generates a thermal barrier between the ionized gas flow and the skin 100.

In yet another embodiment, skin and tissue treatment using the microwave treatment apparatus is combined with light radiation (with reference to FIG. 3). Light is supplied to be radiated to the skin 1 under the footprint of the ionized gas flow, and may be in the wavelength range of 430-1100 nm. Simultaneous exposure of the skin 100 to microwave heating, discharge and light may provide a synergistic effect in acne and skin disease treatment.

In order to perform safe and high-quality treatment of a patient's body part having a complicated three-dimensional structure (for example, the face), a user confirms the size profile of the skin of the body part to be treated, identifies skin regions to be treated, and allocates residence times and microwave and gas parameters to all the skin regions to be treated.

As shown in FIGS. 4 and 5, the robot platform 8 performs automatic positioning and movement of the assembly including the chamber 2, the electrode 1 and the light sources 5 and 5' along the three-dimensional size profile of the skin within the identified skin regions depending on the allocated parameters.

Through additional tilting mechanisms W1 and W2, the ionized gas flow may contact the skin almost perpendicularly to the skin, and the ionized gas flow is moved from a skin region to be treated or the position of the robot platform 8 outside the body part to the next skin region to be treated.

The protective strip 5e' may be adhered to an eye or other sensitive body parts or a skin part during manual or automatic skin treatment, and the protective strip 5e' may be formed of foam so as to protect the body part from convective heating.

The protective strip 5e' may include an electrically conductive layer (i.e., a wire mesh) so as to provide local protection from the microwave energy, may be grounded, and may be adhered to the light-transmitting glass plate 5g' so as to be disposable.

The microwave treatment apparatus according to the present invention may be used not only to treat tissues without the skin but also to treat chronic wounds, particularly to treat skin ulcers caused by diabetes and venous stasis. Such treatment may reduce bacteria clustering around a wounded area and improve blood circulation of basal tissues.

TEST EXAMPLES

The portable microwave treatment apparatus according to the present invention was used to treat the surface of the skin contaminated with *Escherichia coli* bacteria. The parameters of the microwave treatment apparatus are as follows.

The diameter of the electrode 1 was 6 mm, the length of the electrode 1 was 100 mm, the inner diameter of the chamber 2 was 18 mm, the length of the chamber 2 was 95 mm, the distance from the closed end of the chamber 2 to a portion of microwaves connected to the electrode 1 was 15 mm, the electrode 1 and the chamber 2 were formed of brass, the frequency of the microwaves was 1.12 GHz, and the power of the microwaves was 50 W.

Ar was used as compressed gas, and the flow velocity of the compressed gas was 5 s/m. The distance D1 was 15 mm, and a treatment time was 10 sec. It was observed that the number of surviving *Escherichia coli* bacteria was decreased.

As is apparent from the above description, a microwave treatment apparatus according to the present invention may stimulate the skin and subcutaneous tissues using various types of stimuli, thereby being capable of increasing curative effects.

Particularly, the microwave treatment apparatus according to the present invention may treat the surface of the skin or the subcutaneous tissues using a combination among a microwave frequency electric field generated by microwaves, low-frequency electric spark discharge, low-temperature ionized gas flow, and light, thereby further increasing curative effects.

Although the preferred embodiments of the present invention have been disclosed for illustrative purposes, those skilled in the art will appreciate that various modifications, additions and substitutions are possible, without departing from the scope and spirit of the invention as disclosed in the accompanying claims.

The invention claimed is:

1. A microwave treatment apparatus configured to treat skin or subcutaneous tissues, the microwave treatment apparatus comprising:
    an electrode configured to generate microwaves by electricity received from a power supply;
    a chamber having a tubular hollow and disposed at a central region of the microwave treatment apparatus configured to expose one end of the electrode towards the skin; and
    a gas supply source configured to supply gas to a space between the electrode and an inner wall of the chamber,
    wherein the supplied gas is converted into ionized gas by an electric field having frequencies of the microwaves generated by the electrode, and the microwave treatment apparatus is configured to supply the ionized gas to the skin so that the skin is exposed to the ionized gas,
    wherein temperature of the ionized gas is equal to or less than 50° C.,
    wherein the ionized gas is configured to treat a region of the skin having a depth less than 10 mm,
    wherein a flow frequency of the ionized gas is repeatedly modulated from a lower level to a higher level with 0.001-10 Hz,
    wherein a subsidiary gas supply source is further disposed at one side of the microwave treatment apparatus,
    wherein a nozzle is disposed adjacent to an open end of the chamber, a valve is disposed on a gas line between the nozzle and the subsidiary gas supply source, and an outlet of the nozzle is configured to be disposed to head towards an intersection between the skin and a central axis of the chamber, the central axis of the chamber being configured to be disposed between the electrode and the skin,
    wherein at least one light source configured to radiate light to the skin comprises a first light source and a second light source,
    wherein the first light source is installed on a light source holder integrated with one side of the chamber,
    wherein the second light source is configured to be installed at one end of the chamber opposite to the skin, a light-transmitting glass plate is installed at the one end of the chamber, a lens is installed at the one end of the chamber, and the lens is installed between the second light source and the light-transmitting glass plate,
    wherein the microwave treatment apparatus is configured to be installed in a treatment apparatus holder, and the treatment apparatus holder is installed to be supported by an assembly base so as to be movable vertically and to be movable horizontally in an arc shape, and
    wherein the treatment apparatus holder is installed so as to be movable horizontally in the arch shape along an arc-shaped rail, and elevating slides are installed at both ends of the arc-shaped rail so as to move the treatment apparatus holder vertically, and are combined, so as to be movable vertically, with an open front part of the assembly base having an inner space configured such that a human body is placed therein.

* * * * *